United States Patent [19]

Sato

[11] 4,320,978
[45] Mar. 23, 1982

[54] INTEGRATION SPHERE TYPE TURBIDIMETER

[75] Inventor: Ko Sato, 2-6 Fukazawa 6 chome, Setagaya-ku, Tokyo, Japan

[73] Assignees: Ko Sato; Nippon Precision Optical Instrument Co., Ltd., both of Tokyo, Japan

[21] Appl. No.: 96,235

[22] Filed: Nov. 20, 1979

[30] Foreign Application Priority Data

Dec. 12, 1978 [JP] Japan .................................. 53-152697

[51] Int. Cl.³ ..................... G01N 21/51; G01N 21/53; G01V 1/00
[52] U.S. Cl. .................................. 356/440; 250/228; 356/442
[58] Field of Search ........................ 356/440, 436–443, 356/445–448, 339; 250/228, 574

[56] References Cited

U.S. PATENT DOCUMENTS

| | | | |
|---|---|---|---|
| 3,838,926 | 10/1974 | Kato et al. | 250/228 |
| 3,861,198 | 1/1975 | Shea | 350/63 |
| 4,152,070 | 5/1979 | Kushner et al. | 356/343 |
| 4,165,179 | 8/1979 | Sato | 350/61 |
| 4,186,838 | 2/1980 | Levitt et al. | 250/228 |
| 4,240,752 | 12/1980 | Tausch et al. | 356/436 |

FOREIGN PATENT DOCUMENTS 479662  2/1938  United Kingdom ................ 356/341

Primary Examiner—William H. Punter
Attorney, Agent, or Firm—Kurt Kelman

[57] ABSTRACT

An integration sphere type turbidimeter having a cylindrical sample cell passing through an integration sphere and an optical system disposed so as to permit a collimated beam of light to be projected into the sample cell from one end to the other end thereof, whereby the diffused rays of light produced by the dispersed particles in the sample liquid are substantially completely picked up by the integration sphere.

4 Claims, 2 Drawing Figures

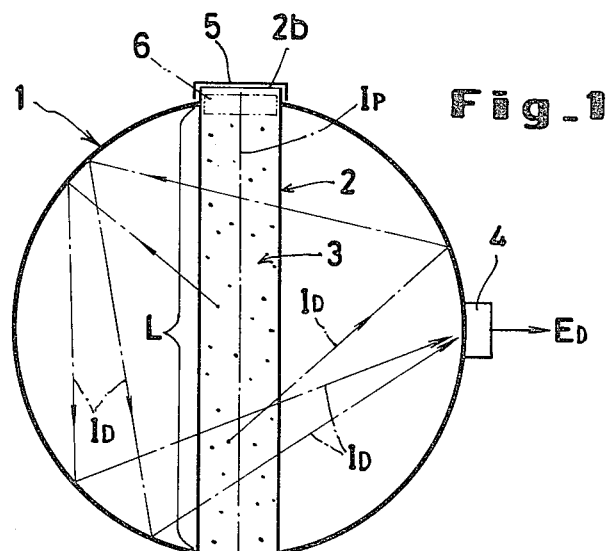
Fig_1
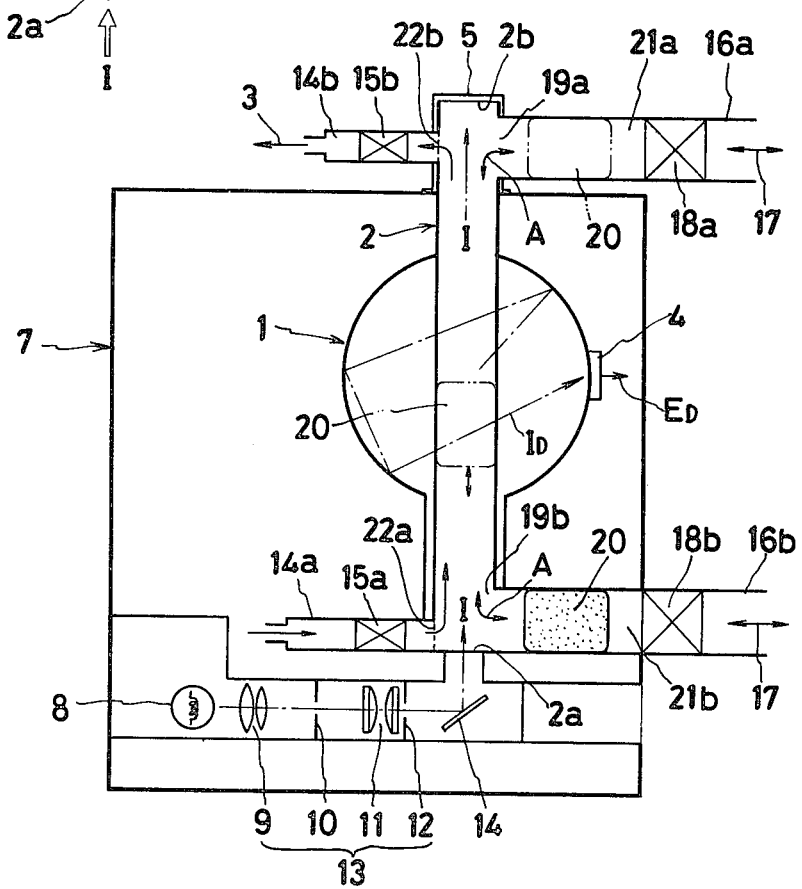
Fig_2

INTEGRATION SPHERE TYPE TURBIDIMETER

BACKGROUND OF THE INVENTION

This invention relates to an integration sphere type turbidimeter capable of measuring the turbidity of a sample liquid accurately by the optical diffusion method even when the sample liquid contains dispersed particles of an extremely small particle diameter in an extremely low concentration.

Generally, the conventional integration sphere type turbidimeter comprises an integration sphere, a sample cell disposed outside the integration sphere and adapted to hold a given sample liquid therein, an optical device for passing a collimated beam of light through the sample cell into the integration sphere, and a light receiving element disposed on the integration sphere and adapted to pick up diffused light resulting from the impingement of a part of the collimated beam of light upon the dispersed particles of the sample liquid in the sample cell and, further comprises another light receiving element to pick up the part of the collimated beam of light which passes through the sample cell, whereby the turbidity of the sample liquid is determined by comparing the amounts of light picked up by the two light receiving elements mentioned above (British Pat. No. 1,089,848 and U.S. Pat. No. 4,165,179, for example). In the conventional turbidimeter wherein the sample cell is disposed outside of the integration sphere and the collimated beam of light passes through the sample cell and then into the sphere, the maximum amount of diffused light that can possibly enter the integration sphere is that falling within the range of 180° of the sample cell on the integration sphere side, this maximum being realized when the sample cell is in direct contact with the integration sphere. Enlargement of the sample cell does not help to increase the amount of diffusee light received by the integration sphere since the turbidimeter can measure turbidity only in the portion penetrated by the incident collimated beam of light and, consequently, the region which produces the light diffusion is not a function of cell size. As a result, the conventional turbidimeter has been unable to provide effective measurement of turbidity where the sample liquid contains dispersed particles having a diameter on the order of $1\mu$ at a low concentration of less than 500 ppb, for example.

As a way of overcoming this problem, it might be thought that the extreme smallness of the amount of diffused light picked up by the light receiving element could be compensated for by greatly increasing the gain of the amplifier system connected to the output terminal of the photo-electric conversion element which picks up the diffused light. This would be a false assumption, however, since when the gain is increased past a certain level and the input is of extremely small magnitude, there ensure problems relating to linearity and amplification ratio. In the first place, the relationship between light received and electrical output of the photoelectric conversion element has poor linearity when the amount of light picked up is very small. An attempt to eliminate this difficulty electrically by the adoption of a compensatory circuit would call for enormous amounts of effort and expense and would add greatly to the complexity of the measuring system.

The needs of industry on the other hand are no longer met by the actual performance of conventional turbidimeters. As a consequence, there has arisen a need to develop a turbidimeter which is capable of measuring, accurately to within a graduation as fine as 50 ppb, extremely low degrees of turbidity such as in sample liquids having dispersed therein very minute particles having a particle diameter of less than $0.5\mu$, for example.

The object of this invention is to provide a turbidimeter capable of accurately measuring extremely low degrees of turbidity.

SUMMARY OF THE INVENTION

To accomplish the object described above according to the present invention, there is provided a turbidimeter which has a cylindrical sample cell pierced through an integration sphere and a light source unit disposed so that a collimated beam of light is passed through the sample cell interior from one end to the other end of the cell.

The light impinging on the dispersed particles in a sample liquid in the sample cell are diffused in all directions throughout the entire length of the sample cell. Since the sample cell is disposed within the integration sphere, the diffused light issuing from the dispersed particles is wholly received by the light receiving element disposed within the integration sphere. The turbidimeter, therefore, determines the turbidity of a given sample liquid on the basis of all diffused light issuing from the whole of the sample cell. Even when the sample liquid possess a very low degree of turbidity, the turbidimeter is capable of measuring the turbidity with high accuracy.

The other objects and characteristics of the present invention will become apparent from the further disclosure of the invention to be given hereinafter with reference to the accompanying drawing.

BRIEF EXPLANATION OF THE DRAWING

FIG. 1 is an enlarged view of the essential part of the integration sphere type turbidimeter according to the present invention.

FIG. 2 is a schematic explanatory diagram of the integration sphere type turbidimeter according to this invention.

DESCRIPTION OF PREFERRED EMBODIMENT

Referring to FIG. 1, a sample cell 2 passes through the interior of an integration sphere 1 with its axis coincident to a diameter of the sphere. A collimated beam of light "I" is projected into a sample within the sample cell 2 in the longitudinal direction of the sample cell from one end 2a to the other end 2b of the sample cell 2, namely, in the diametric direction of the integration sphere. This is different from the conventional turbidimeter wherein the collimated beam is projected from outside the integration sphere perpendicularly to the externally disposed sample cell.

The diameter of the collimated beam "I" is desired substantially to equal the inside diameter of the sample cell 2. At any rate, owing to the aforementioned arrangement, the rays of light $I_D$ are diffused by the dispersed particles in the sample liquid 3 (indicated by chain dotted lines) in all the radial directions (360°) of the sample cell and, after numerous reflections and diffusions are eventually picked up without any loss by the diffused light receiving element 4 disposed on the inner wall surface of the integration sphere. Further, since the surface area of the cell from which the diffused rays of light $I_D$ issue covers the entire length "L"

of the sample cell embraced within the integration sphere, the amount of diffused light picked up and the volume of information on the diffused rays of light collected by this turbidimeter are notably larger than in the case of the conventional turbidimeter wherein the incident collimated beam of light is locally introduced and the diffused rays of light issue only from the local region.

Even when the absolute value of the turbidity of a given sample liquid 3 is extremely low, therefore, the region subjected to measurement is so large as to extend throughout the entire length of the cell because the collimated beam "I" is introduced in the longitudinal direction of the sample cell. Even if the diffusion of light occurring in each limited segment of the whole region available for the measurement is very small, the amount of diffused light generated throughout the entire length of the sample cell is considerable over the whole length of the cell. Moreover, the fact that the diffused rays $I_D$ issuing in all the directions (360°) are eventually received by the light receiving element 4 adds greatly to the accuracy of the measurement.

The embodiment of the invention shown in FIG. 1 does not employ a second light receiving element as is adopted in the conventional turbidimeter for the purpose of picking up the part of the collimated beam $I_P$ whch passes through the cell without being diffused. This is because the turbidimeter of the present invention is aimed specifically at measuring extremely low degrees of turbidity. In the range of turbidity not exceeding the level of 50 ppb, for example, a change in turbidity on the order of some 10's of ppb, causes no substantial difference in the amount of light passing through the cell without being diffused. Thus, provision of such a second light receiving element to pick up the beam passing through the cell is not required. Conversely, in the case of the measurement of extremely low degrees of turbidity, it is desirable that the turbidimeter be provided with a light trap 5 adapted to completely absorb the part of beam $I_P$ advancing to the outlet end 2b of the sample cell 2 lest this light be reflected or diffused and sent back toward the sample liquid 3.

Notwithstanding the specific construction described above, the turbidimeter of the present invention can be effectively used for the measurement of high degrees of turbidity as well. Also in this case, the measurement can be accomplished with high sensitivity and resolvability. Specifically, in order for the turbidimeter to be utilized for the measurement of high degrees of turbidity with enhanced sensitivity and resolvability, it is required to be provided at the outlet end of the sample cell with a light receiving element 6 as indicated by a chain dotted line in FIG. 1. In this case, since the turbidimeter has very high sensitivity at low turbidity levels, some of the component elements which make up the turbidimeter may need modification where liquids predominantly subjected to the measurement have such degrees of turbidity that fall outside the range of turbidity prescribed for this turbidimeter.

The shape of the sample cell 2 is optional. Specifically where the turbidimeter is utilized for the measurement of extremely low degrees of turbidity, however, the sample cell is in a cylindrical shape in order to curb the possible diffusion of light on the wall surface of the cell. As the material for the sample cell, a hard glass such as "Pyrex" can be used advantageously as in the conventional turbidimeter.

In the present invention, since the diffused rays of light produced by the dispersed particles in the sample liquid are reflected by the inner wall surface of the integration sphere and are substantially completely picked up by the light receiving element 4, the amount of dispersed light picked up is fairly large even in the case of a sample liquid of very low turbidity. Consequently, the light receiving element 4 can be operated at a point of high linearity and the output of electricity of conversion Ed is not different from that used in the conventional turbidimeter. The type of electrical measuring system which is connected to the conventional turbidimeter, therefore, can be used practically in its unmodified form for the turbidimeter of the present invention.

Now, the turbidimeter according to the present invention will be specifically described with reference to FIG. 2.

The integration sphere 1 is set in position within a housing 7 and the sample cell 2 is disposed to pass through the integration sphere. The collimated beam "I" is projected into the sample cell 2 via one end 2a of the sample cell. In this case, the collimated beam "I" adjusted to a desired diameter is obtained by allowing the light from a light source 8 such as of an incandescent bulb to be passed through an optical system 13 for the formation of a collimated beam which consists of a condenser lens system 9, a pinhole 10, a collimator lens 11 and a mask 12. The collimated beam so produced is projected into the cell 2 through the end 2a with the aid of a reflecting mirror 14. The aforementioned arrangement of component elements has been adopted for the purpose of preventing the size of the turbidimeter from being needlessly increased in its vertical direction. Where no such special consideration is required, the light source 8 and the optical system 13 may be disposed at positions such that the collimated beam is projected straight into the sample cell 2 through the end 2a.

Since the diameter of the collimated beam is desired to be roughly equal to the diameter of the sample cell, it is proposed herein to adopt an incandescent light with a view to facilitating to formation of a collimated beam of a desired diameter as much as possible. Where some complication of the lens system is tolerable, a monochrome laser beam of high coherency may be effectively used instead.

In the embodiment of FIG. 1, the sample cell 2 is illustrated as designed for sealing in a given sample 3. The sample cell 2, otherwise, may be designed in the form of a flow type cell as illustrated in FIG. 2. The flow type cell may be provided near the lower end thereof with an influent port 14a for the incoming sample liquid 3 and near the upper end thereof with a discharge port 14b for the outgoing sample liquid, whereby the sample liquid continuously flowing through the cell can be subjected to measurement. Otherwise, valve means 15a, 15b such as solenoid valves may be disposed in the respective ports 14a, 14b and operated so that one batch of sample liquid can be discharged from the cell and another fresh sample of liquid introduced into the cell after each measurement.

The sample cell 2 may also be provided at the upper and lower ends thereof respectively with influent ports 16a, 16b for admitting clean water 17 under pressure, whereby the clean water may be sent alternatingly through the cell by selective operation of valve means 18a, 18b provided respectively inside the ports 16a, 16b, for the purpose of cleaning the cell interior.

Further, in the portions 19a, 19b respectively of the effluent and influent ports 16a, 16b which open into the sample cell, cavities 21a, 21b of a diameter roughly equal to the diameter of the sample cell may be formed in front of the solenoid valves 18a, 18b for accommodating therein a wiper 20 made of a spongy substance capable of being swelled with absorbed liquid. By causing the fluid 17 such as water to be alternatingly passed through the cell interior and consequently allowing the wiper 20 to move alternatingly within the cavities 21a, 21b via the intervening cell interior while strongly rubbing the inner wall surface of the cell, the impurities adhering fast to the cell interior can be easily removed. In this arrangement, the possibility of the wiper accidentally entering the ports 14a, 14b for the sample liquid can be eliminated by giving these ports a sufficiently small diameter or by disposing screen means 22a, 22b at the portions 19a, 19b communicating with the cell interior and allowing the screen means to serve as stoppers for the wipers 20. In the illustrated embodiment, the wipers 20 are required to change their directions of motion substantially at right angles as indicated by the arrow "A" where the effluent and influent ports 16a, 16b are joined into the sample cell. When the wiper is made of a spongy substance, it can make the aforementioned change in the directions of motion without any difficulty. Optionally the joined portions can be modified to impart a smooth curve thereto and smoothen the motion of the wiper through the bends.

When the sample liquid subjected to measurement by the turbidimeter has extremely low turbidity, impurities which adhere to the inner wall surface of the sample cell may possibly affect the accuracy of measurement. It is, therefore, critical for the performance of the turbidimeter of this invention that the sample cell should be constructed so as to be easily cleaned.

The embodiment of FIG. 2, represents a turbidimeter to be used specifically for the measurement of extremely low degrees of turbidity. For the reason previously touched upon, therefore, the light receiving element 4 for the diffused rays $I_D$ alone is provided and no light receiving element for the penetrating beam $I_P$ is provided and instead a light trap 5 is incorporated to absorb the penetrating beam. Depending on the nature of the liquids to be measured, however, the turbidimeter may be provided with an additional light receiving element to be used specifically for picking up the penetrating beam.

Now, a working example of the turbidimeter according to the present invention will be described. For referential purposes, the performance of this turbidimeter is compared in the following table with that of the conventional turbidimeter having a sample cell disposed outside the integration sphere.

|  | Turbidimeter of this invention | Conventional turbidimeter |
| --- | --- | --- |
| Diameter of integration sphere | 50 mm | 50 mm |
| Diffused light receiving element | Silicon photo-diode | Silicon photo-diode |
| Output signal of element | 0 to 10 mV | 0 to 10 mV |
| Light source | 30 W of incandescent bulb | 30 W of incandescent bulb |
| Sample cell |  |  |
| Type | Flow type | Flow type |
| Shape | Cylindrical | Rectangular |

-continued

|  | Turbidimeter of this invention | Conventional turbidimeter |
| --- | --- | --- |
| Material | Pyrex | Pyrex |
| Size | 10 mm in inside diameter, about 3.9 cm$^3$ of inner volume | 30 mm × 30 mm × 7 mm, about 3.9 cm$^3$ of inner volume |
| Maximum resistance to pressure | 5 Kg/cm$^2$ | 5 Kg/cm$^2$ |
| Volume of sample penetrated by collimated beam | about 0.98 cm$^3$ | about 0.98 cm$^3$ |
| Surface area of cell emitting diffused light | about 7.85 cm$^2$ | about 0.196 cm$^2$ |

When a sample liquid containing dispersed particles at a concentration of 50 ppb was tested for its turbidity by the turbidimeter of this invention having the specifications indicated above, the light receiving element issued a maximum output signal with a full-span error of less than 3%. In the case of the conventional turbidimeter, the maximum output signal was obtained effectively with sample liquids containing dispersed particles at concentrations of more than 500 ppb. This means that when the two turbidimeters are constructed by using component elements possessing virtually the same specifications, the turbidimeter of this invention enjoys about ten times more sensitivity than the conventional turbidimeter.

As described above, this invention aims to improve on the conventional turbidimeter not by an improvement in the performance of the electric processing system but by providing a substantial improvement in the function of the turbidimeter as a whole. Thus, the turbidimeter of the present invention promises great usefulness and contributes greatly to various industrial field which indicate the needs of using liquids which have extremely low degrees of turbidity.

What is claimed is:

1. An integration sphere type turbidimeter comprising
   (a) an integration sphere having a diameter and two diametrically opposed openings along the diameter;
   (b) a cylindrical sample cell disposed along the diameter and having two ends passing through the opposed sphere openings, the cell containing
      (1) a sample liquid having dispersed therein particles of a diameter of less than one micron at a concentration of less than 500 ppb;
   (c) means projecting a collimated beam of light into the cylindrical cell from one end of the cell to the other end thereof, the collimated light being diffused in the cell by the dispersed particles;
   (d) a light trap at said other end of the cylindrical sample cell; and
   (e) a light receiving element disposed in the integration sphere for receiving the diffused light from the cylindrical sample cell.

2. The turbidimeter of claim 1, further comprising means for passing the sample liquid into the cell through one of the ends and discharging the liquid through the other end.

3. The turbidimeter according to claim 1 or 2 wherein the collimated beam of light projected into the sample cell has a cross section identical to the inside cross section of the sample cell.

4. The turbidimeter of claim 2, further comprising means for passing water under pressure into the cell through one of the ends and discharging the water therefrom through the other end for washing the cell.

* * * * *